US00PP07944P

United States Patent [19]

Warriner

[11] Patent Number: Plant 7,944

[45] Date of Patent: Aug. 18, 1992

[54] ROSE PLANT JACBRITE

[75] Inventor: William A. Warriner, Tustin, Calif.

[73] Assignee: Bear Creek Gardens, Inc., Medford, Oreg.

[21] Appl. No.: 625,914

[22] Filed: Dec. 10, 1990

[51] Int. Cl.[5] ..... A01H 5/00

[52] U.S. Cl. ..... Plt./11

[58] Field of Search ..... Plt./1, 11, 12, 13

[56] References Cited

U.S. PATENT DOCUMENTS

P.P. 682 4/1946 Roberts ..... Plt. 11
P.P. 1,945 5/1960 Fisher ..... Plt. 11
P.P. 4,620 1/1981 Winchel ..... Plt. 11
P.P. 6,863 6/1989 Perry ..... Plt. 12

*Primary Examiner*—Howard J. Locker
*Attorney, Agent, or Firm*—Klarquist, Sparkman, Campbell, Leigh and Whinston

[57] ABSTRACT

A hybrid tea class rose plant having novel, very bright yellow flowers that are tipped in red, the red intensifying and spreading across the upper side of the petal as it ages, smooth rachises with many glands at their bases, smooth stipules having edges with many glands, and thick leathery petals.

1 Drawing Sheet

1

The present invention relates to a new and distinct variety of rose plant of the hybrid tea class which was originated by me by crossing the variety JAChad, U.S. Plant Pat. No. 6,317, with an unnamed seedling.

The primary objective of this breeding was to produce a new rose variety having the interesting orange and yellow coloration of JAChad but with the much greater yellow color intensity of the unnamed male parent. The objective was substantially achieved along with other desirable improvements as evidenced by the following unique combination of characteristics which are outstanding in the new variety and which distinguish it from its parents, as well as from all other varieties of which I am aware:

1. Novel, very bright yellow flower that is tipped in red. This red intensifies and spreads across the upperside of the petals as it ages.
2. Smooth rachis with many glands at its base.
3. Smooth stipules with edges having many glands.
4. Thick leathery petals.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with the Royal Horticultural Society (London) Colour Chart, except where ordinary dictionary significance of color is indicated.

Parentage:

*Seed parent.*—JAChad, U.S. Plant Pat. No. 6,317.

*Pollen parent.*—Unnamed seedling.

Classification:

*Botanical.*—*Rosa hybrida.*

*Commercial.*—Hybrid tea.

2

FLOWER

Observations made from specimens grown in a garden in Somis, Calif. in September, 1990.

Blooming habit: Recurrent.

Bud:

*Size.*—1¾ inches when the petals start to unfurl.

*Form.*—Long, pointed ovoid.

*Color.*—When sepals first divide, bud color is Yellow-orange Group 14A, tipped with Red Group 45C. When half blown, the upper sides of the petals are Yellow Group 14A, with an expanding area of Red Group 45C; and the lower sides of the petals are Yellow Orange Group 14A; Red Group 45C where exposed to light.

*Sepals.*—Color: Green Group 138C. Surface texture: Covered with fine hairs. There are three normally appendaged sepals with glands on sepal edges. There are two unappendaged sepals with hairy edges.

*Receptacle.*—Color: Green Group 138B. Shape: Funnel. Size: Medium (⅜×⅜"). Surface: Smooth.

*Peduncle.*—Length: Short (2"). Surface: Prickly and glandular. Color: Bronzy. Strength: Stiff, erect.

Bloom:

*Size.*—Large. Average open size is 5 inches.

*Borne.*—Singly.

*Stems.*—Medium (14 to 18").

*Form.*—When first open: High center. Permanence: Retains its form to the end, outer petals curl back.

*Petalage.*—Number of petals under normal condition: 20 to 25.

*Color.*—The upper side of the petals is Yellow Orange Group 14A tipped with Red Group 45C. The reverse side of the petals is Yellow Group 14A. The base of petals is Yellow Group 14A. The major color on the upper side is Yellow Group 14A.

*Variegations.*—None.

*Discoloration.*—Little change in the general tonality at the end of the first day. At the end of the third day, gradual intensification of the red coloration on the petal surface as the flower ages.

*Fragrance.*—Slight.

Petals:

*Texture.*—Thick, leathery.

*Shape.*—Round to deltoid.

*Form.*—Tips slightly recurved, edges slightly quilled.

*Arrangement.*—Imbricated. Petaloids in the center: Few.

*Persistence.*—Drop off cleanly.

*Lastingness.*—On the plant: Long (5 to 6 days). As a cut flower: Long (5 to 7 days).

Reproductive parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: Reddish.

*Stigmas.*—Color: Yellow.

Form: Bush.

Growth: Vigorous, upright, branching. Growth tends to be upright and angular.

Foliage:

*Number of leaflets on normal mid-stem leaves.*—5.

*Size.*—Large (5½ by 4½").

*Quantity.*—Normal.

*Color.*—New foliage: Reddish. Old foliage: Dark green.

Leaflets:

*Shape.*—Pointed oval.

*Texture.*—Upper side: Smooth.

*Edge.*—Serrated.

*Serration.*—Single, small.

*Petiole rachis.*—Color: Reddish.

*Petiole underside.*—Smooth, but with many glands on the rachis base.

*Stipules.*—Medium (9/16"), smooth but edged with many glands.

*Disease resistance.*—Susceptible to mildew but resistant to rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅜"), hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its unique bright yellow flower color that is tipped in red, the gradual spread of this red coloration across the whole flower petal upper surface as it ages while the reverse of the petal stays yellow unless exposed to the sun, and the presence of many glands on the otherwise smooth stipule edges and on the bases of the rachises.

* * * * *

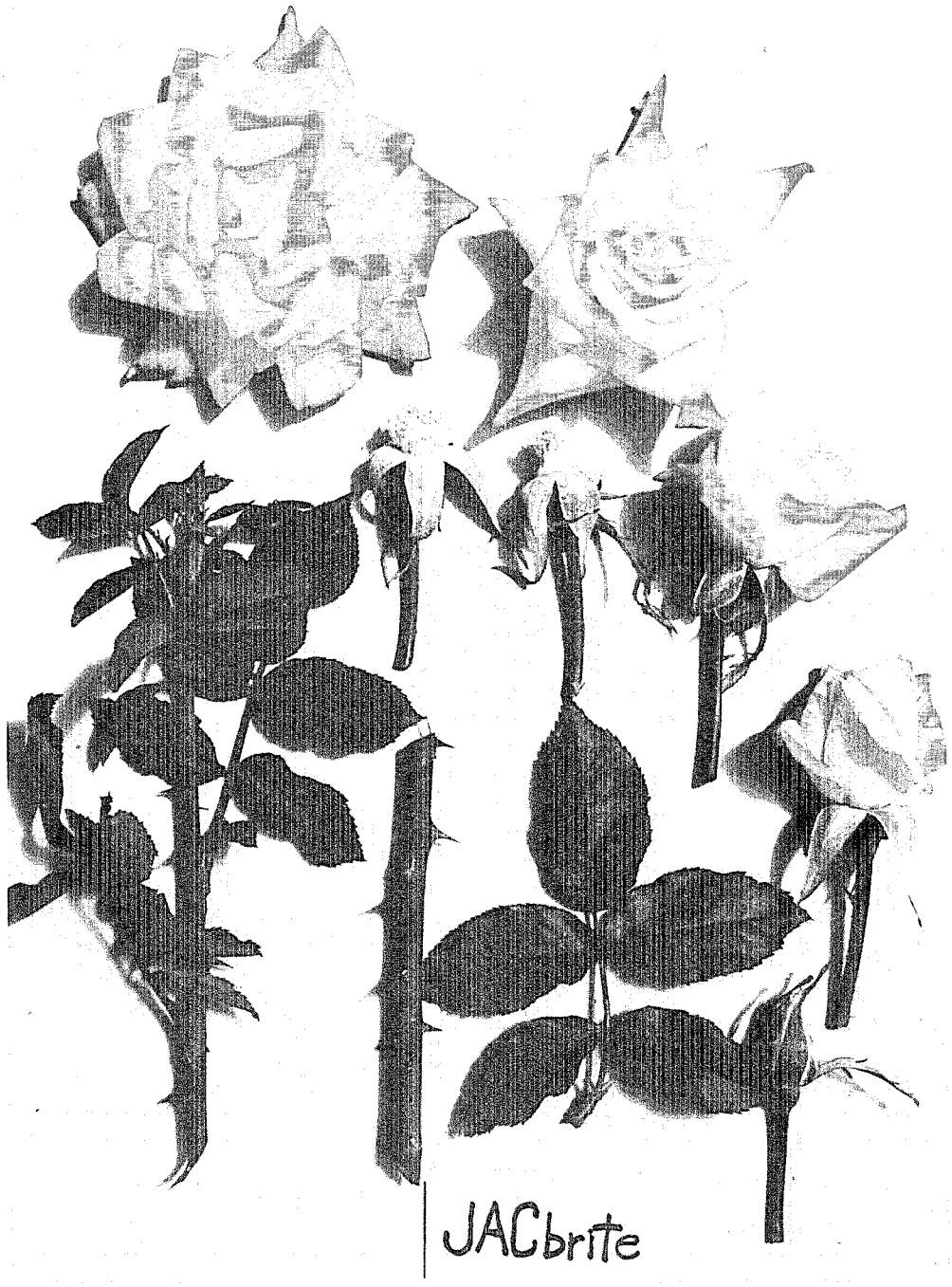
JACbrite